(12) United States Patent
Podrebarac et al.

(10) Patent No.: US 6,919,016 B2
(45) Date of Patent: Jul. 19, 2005

(54) PROCESS FOR THE UTILIZATION OF REFINERY C4 STREAMS

(75) Inventors: Gary G. Podrebarac, Houston, TX (US); Mario J. Maraschino, Houston, TX (US)

(73) Assignee: Catalytic Distillation Technologies, Pasadena, TX (US)

( * ) Notice: Subject to any disclaimer, the term of this patent is extended or adjusted under 35 U.S.C. 154(b) by 0 days.

(21) Appl. No.: 10/912,253

(22) Filed: Aug. 5, 2004

(65) Prior Publication Data

US 2005/0010071 A1 Jan. 13, 2005

Related U.S. Application Data

(62) Division of application No. 10/055,196, filed on Jan. 23, 2002, now Pat. No. 6,849,773.

(51) Int. Cl.[7] .............................. C10L 1/04; C10G 45/58
(52) U.S. Cl. .............................. 208/16; 208/56; 208/58; 585/331; 585/332
(58) Field of Search .............................. 208/16, 58, 56; 585/331, 332

(56) References Cited

U.S. PATENT DOCUMENTS

| | | |
|---|---|---|
| 3,895,049 A * | 7/1975 | Umemura et al. .......... 558/324 |
| 3,960,978 A | 6/1976 | Givens et al. |
| 4,021,502 A | 5/1977 | Plank et al. |
| 4,150,062 A | 4/1979 | Garwood et al. |
| 4,211,640 A | 7/1980 | Garwood et al. |
| 4,227,992 A | 10/1980 | Garwood et al. |
| 4,242,530 A | 12/1980 | Smith, Jr. |
| 5,087,780 A | 2/1992 | Arganbright |
| 5,510,568 A | 4/1996 | Hearn |
| 6,169,218 B1 | 1/2001 | Hearn et al. |
| 6,242,661 B1 | 6/2001 | Podrebarac et al. |
| 6,274,783 B1 | 8/2001 | Gildert et al. |
| 6,333,442 B1 * | 12/2001 | Cosyns et al. .............. 585/332 |

* cited by examiner

*Primary Examiner*—Thuan D Dang
(74) *Attorney, Agent, or Firm*—Kenneth H Johnson

(57) ABSTRACT

A process is disclosed for preparing a $C_4$ stream for feeding to an alkylation process which reacts isobutane with butene to produce isooctane. The $C_4$ stream is treated in a first distillation column reactor to remove dienes and mercaptans and separate out any $C_5$'s which might be present. The treated $C_4$'s are then fed to a second distillation column reactor that concurrently isomerizes 1-butene to 2-butene and splits the normal $C_4$'s from the iso $C_4$'s. The iso $C_4$'s are then fed to a third distillation column reactor where a portion of the isobutene is saturated to isobutane. The $C_4$'s from the isomerization/splitter are combined with the $C_4$'s from the hydrogenation unit and fed to a cold acid alkylation unit. The third distillation column may also oligomerize a portion of the isobutene to diisobutene in the upper end which is saturated in the bottom of the column to isooctane.

7 Claims, 2 Drawing Sheets

PROCESS FOR THE UTILIZATION OF REFINERY C4 STREAMS

This is a division of application Ser. No. 10/055,196 filed on Jan. 23, 2002 now U.S. Pat. No. 6,849,773 present invention relates to a process for the utilization of refinery $C_4$ streams containing iso and normal butanes and butenes. More particularly the invention relates to a process for producing alkylate feed from a mixed $C_4$ stream. In one embodiment the invention relates to a process which produces isooctane in addition to alkylate feed.

BACKGROUND OF THE INVENTION

Field of the Invention

Related Information

Refinery $C_4$ streams have recently been utilized in the production of methyl tertiary butyl ether (MTBE) for use as an oxygenate additive and octane improver in motor gasolines. Processes and catalyst systems for their use in this manner have been developed over the years and include U.S. Pat. Nos. 4,215,011; 4,242,530; 4,232,177; 4,307,254; 4,336,407; 4,375,576 and like patents.

Refinery $C_4$ streams have also been used as the source of butenes and isobutane for feed to cold acid alkylation processes which produce isooctane. Generally there has been an imbalance in the amount of isobutene and butenes in refinery $C_4$ streams which have led to the use of the MTBE processes which utilize the isobutene, effectively removing it from the $C_4$ stream.

Environmental concerns have led at least the state of California to ban the use of MTBE in gasoline. Other processes for the balancing of the iso/normal butenes are now required.

SUMMARY OF THE INVENTION

Briefly, the present invention is an integrated process for the preparation of paraffin alkylate in which a $C_4$ hydrocarbon feed is first treated to remove dienes and mercaptans, for example, by reacting the dienes and mercaptans to form sulfides, separating the $C_4$'s from heavy material comprising the sulfides, for example, by fractionation. The treated $C_4$ feed is then subjected to isomerization to convert butene-1 to butene-2 and the iso $C_4$'s are separated from the normal $C_4$, for example by fractionation. The iso $C_4$ portion is hydrogenated to convert isobutene to isobutane and the $C_4$ fractions reunited and subjected to paraffin alkylation to produce an alkylate comprising isooctane.

In a preferred embodiment the $C_4$ stream is first treated in a first distillation column reactor to remove dienes and mercaptans and separate out any $C_5$'s which might be present. The treated $C_4$'s are then fed to a second distillation column reactor that concurrently isomerizes 1-butene to 2-butene and splits the normal $C_4$'s from the iso $C_4$'s. The iso $C_4$'s are then fed to a third distillation column reactor where a portion of the isobutene is saturated to isobutane. The $C_4$'s from the isomerization/splitter are combined with the $C_4$'s from the hydrogenation unit and fed to a cold acid alkylation unit.

In one embodiment the third distillation column reactor also oligomerizes a portion of the isobutene to diisobutene in the upper end which is saturated in the bottom of the column to isooctane. A portion of the unreacted isobutene is also hydrogenated to isobutane. The remainder of the iso $C_4$'s are fed to alkylation unit.

DETAILED DESCRIPTION OF THE PREFERRED EMBODIMENT

Figure 1:
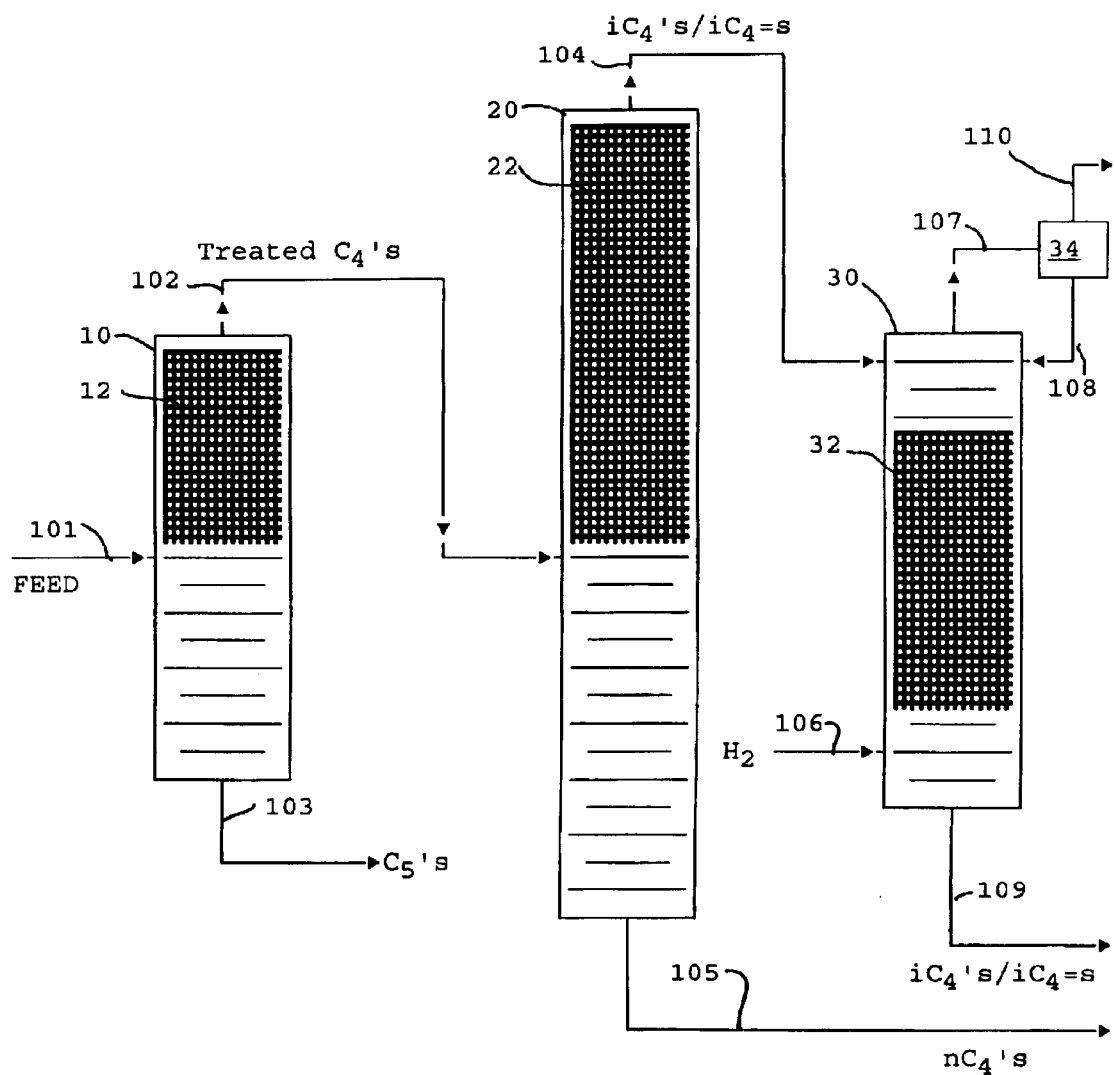
FIG. 1 is a flow diagram in schematic form of one embodiment of the invention.

Referring now to FIG. 1 a flow diagram of one embodiment of the invention is shown. Feed to a cold acid alkylation unit must be low in dienes and mercaptans. To this end the mixed $C_4$ feed in flow line 101 is treated in a distillation column reactor 10 containing a bed 12 thioetherification catalyst which reacts the mercaptans with dienes in the feed to produce higher boiling sulfides which are removed in the bottoms in flow line 103 along with any $C_5$'s in the feed. Alternatively this column may be operated to send the $C_5$'s overhead with the $C_4$'s and to recover the $C_5$'s in the bottoms from column 20 along with the $nC_4$'s in line 105. Catalysts which are useful for this reaction include the Group VIII metals, such as palladium and nickel. Generally the metals are deposited as oxides on an alumina support. The supports are usually small diameter extrudates or spheres. A suitable catalyst for the reaction is 58 wt. % Ni on 8 to 14 mesh alumina spheres, supplied by Calcicat, designated as E-475-SR. Typical physical and chemical properties of the catalyst as provided by the manufacturer are as follows:

TABLE I

| Designation | E-475-SR |
|---|---|
| Form | Spheres |
| Nominal size | 8 × 14 Mesh |
| Ni wt. % | 54 |
| Support | Alumina |

The hydrogen rate to the reactor, which is fed along with the mixed $C_4$ feed in flow line 101, must be sufficient to maintain the reaction which is understood to be the "effectuating amount of hydrogen" as that term is used herein, but kept below that which would cause flooding of the. Generally, the mole ratio of hydrogen to diolefins and acetylenes in the feed is at least 1.0 to 1.0, preferably at least 2.0 to 1.0 and more preferably at least 10 to 1.0.

The catalyst also catalyzes the selective hydrogenation of the polyolefins contained within the feed and to a lesser degree the isomerization of some of the mono-olefins. Generally the relative absorption preference is as follows:

(1) sulfur compounds (2) diolefins (3) mono-olefins

If the catalyst sites are occupied by a more strongly absorbed species, reaction of these weaker absorbed species cannot occur.

The reaction of interest is the reaction of the mercaptans and/or hydrogen sulfide ($H_2S$) with diolefins. In the presence of the catalyst the mercaptans will also react with mono-olefins. However, there is an excess of diolefins to mercaptans and/or hydrogen sulfide ($H_2S$) in the feed and the mercaptans preferentially react with them before reacting with the mono-olefins. The equation of interest which describes the reaction is:

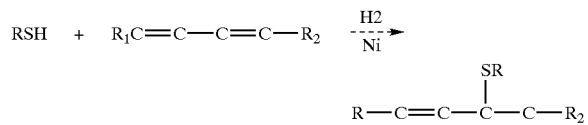

Where R, $R_1$ and $R_2$ are independently selected from hydrogen and hydrocarbyl groups of 1 to 20 carbon atoms. If there is concurrent hydrogenation of the dienes, then hydrogen will be consumed in that reaction. The only mercaptans expected to be present in the mixed $C_4$ feed are the lower boiling ones such as methyl mercaptan.

The treated feed is taken overheads via flow line 102 and then fed to a second distillation column reactor 20 which contains a bed 22 of isomerization catalysts. In the second distillation column reactor 20 the isobutene, isobutane and unreacted 1-butene are concurrently separated from normal butanes and both isomers of 2-butene. Concurrently 1-butene is isomerized to 2-butene to help in the separation. Essentially cis and trans 2-butene and normal butane are removed as bottoms via flow line 105 while the remaining $C_4$'s (isobutane and isobutene) are removed as overheads via flow line 104. The 2-butenes are preferred over 1-butenes for alkylation, since the 2-butene alkylate product has a higher octane number.

The distillation column reactor is generally operated at overhead temperatures in the range of 80 to 180° F., more preferably 100 to 150° F. at pressures in the range of 50 to 110 psig (bearing in mind the effect of pressure on temperature as discussed above). In its more preferred embodiments the present process is operated under conditions, particularly temperature and pressure, which tend to exclude butene-2 from contact with the catalyst while holding the butene-1 in contact with the catalyst. Thus, as butene-1 is isomerized to butene-2 it drops down in the column away from the catalyst and is removed as bottoms.

A reflux is preferably included in the system. The reflux ratio could vary over the rate 0.5:1 to 33:1. In practice, the higher ratio may be used to compensate for a short catalyst bed such as required for experimental work. In commercial size units the catalyst bed would be provided so that lower reflux and hence higher unit productivity could be obtained at lower operating cost. In a modification designed to optimize the operation of the embodiments of both FIG. 1 and FIG. 2 the catalyst bed 22 may be divided into several smaller zones with conventional distillation staging between each zone (not shown).

A catalyst suitable for the present process is 0.5% PdO on $\frac{1}{8}$" $Al_2O_3$ (alumina) extrudates, hydroisomerization catalyst, supplied by Engelhard Industries. The catalyst is believed to be the hydride of palladium which is produced during operation. The hydrogen rate to the distillation column reactor must be sufficient to maintain the catalyst in the active form because hydrogen is lost from the catalyst by hydrogenation. The hydrogen rate must be adjusted such that there is sufficient hydrogen to replace hydrogen lost from the catalyst which is understood to be the "effectuating amount of hydrogen" as that term is used herein but kept below that required for hydrogenation of butenes or to cause flooding of the column. Generally, the mole ratio of hydrogen to $C_4$ hydrocarbon fed to the bed of the present invention will be about 0.01 to 0.60, preferably 0.01 to 0.10.

Another suitable catalyst for the reaction is 0.34 wt % Pd on 7 to 14 mesh $Al_2O_3$ (alumina) spheres, supplied by United Catalysts Inc. designated as G-68C. Typical physical and chemical properties of the catalyst as provided by the manufacturer are as follows:

TABLE II

| Designation | G-68C |
|---|---|
| Form | Sphere |
| Nominal size | 7 × 14 mesh |
| Pd. wt % | 0.3 (0.27–0.33) |
| Support | High purity alumina |

Finally the separated isobutene (along with trace amounts of 1-butene and isobutane) are fed via line 104 to a third distillation column reactor 30 above a bed 32 of hydrogenation catalyst where a portion of the isobutene is saturated to isobutane. Hydrogen for the reaction is fed below the bed via flow line 106. The Pd and Ni catalysts are useful for this hydrogenation also. A distillation is carried out to have a condensing liquid in the column which the hydrogen is occluded which improves the contact between the hydrogen, catalyst and hydrocarbon. Thus an overhead is taken via flow line 107 with the condensible material being condensed in condenser 34 and returned to the distillation column reactor 30 as reflux via flow line 108. Vapors are removed via flow line 110

The bottoms from this distillation column reactor in flow line 109 along with the bottoms from the separation/isomerization column in flow line 105 are fed to a cold acid alkylation process.

Figure 2:
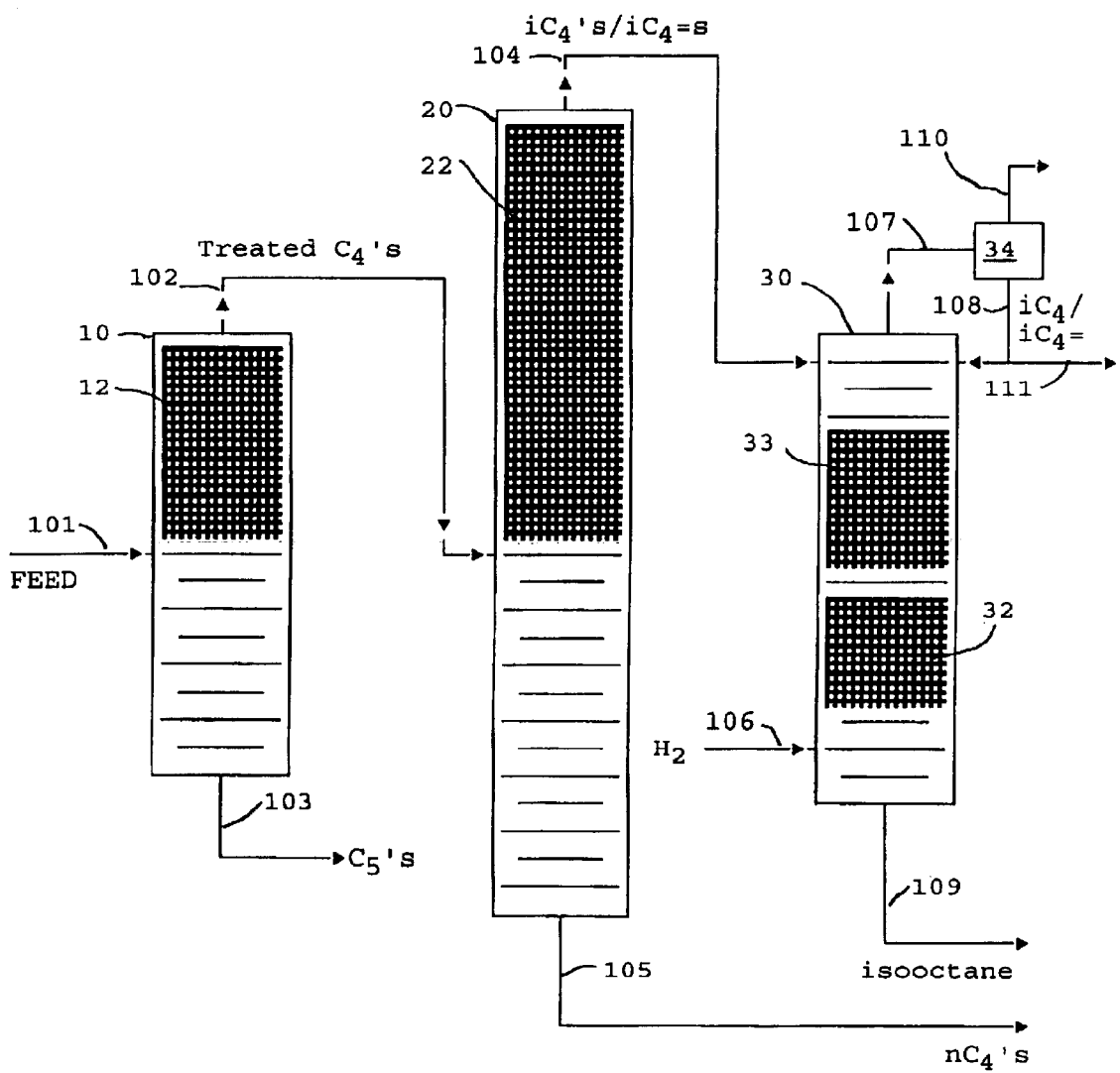
FIG. 2 is a flow diagram in schematic form of a second embodiment of the invention.

Referring now to FIG. 2 a second embodiment of the invention is shown with the same reference numerals depicting the same items as in FIG. 1. The first two distillation column reactors 10 and 20 are identical to that of FIG. 1. The third distillation column reactor 30, however has a bed of acidic cation exchange resin in an upper bed 33 which oligomerizes a portion of the isobutenes to diisobutene which is then hydrogenated in a lower bed of hydrogenation catalyst 32 along with a portion of the isobutene. The hydrogenated diisobutene is 2,2,4-trimethyl pentane or isooctane of 100 octane number and is taken as bottoms via flow line 109. The overheads product containing the $iC_4$'s and $iC_4$='s are taken via flow line 111 and fed to the cold acid alkylation unit (not shown) along with the bottoms from the second distillation column reactor 20.

Preferably the hydrogenation in column 30 is carried out as described in copending U.S. patent application Ser. No. 09/474,192 filed Dec. 29, 1999, which is incorporated herein in its entirety, by concurrently passing the feed containing diisobutene and hydrogen downflow through a reaction zone containing a hydrogenation catalyst at a pressure of less than 300 psig pressure, preferably less than 275 psig, for example less than 200 psig, and for example at least about 100 psig at a temperature within the range of 300° F. to 700° F. to produce an effluent, said temperature and pressure being adjusted such that the temperature of the effluent is above its boiling point and below its dew point, whereby at least a portion but less than all of the material in said reaction zone is in the vapor phase. Preferably the weight hourly space velocity (WHSV), i.e., the weight of petroleum feed per hour per volume of catalyst is greater than 6 $hr^{-1}$, preferably greater than 8 $hr^{-1}$ and more preferably greater than 15 $hr^{-1}$.

The preferred alkylation process comprises alkylation of isoparaffin with olefin comprising contacting a fluid system comprising acid catalyst, isoparaffin and olefin in concurrent flow, preferably downflow into contact in a reaction zone with internal packing, such as, a coalescer under conditions of temperature and pressure to react said isoparaffin and said olefin to produce an alkylate product. Preferably, the fluid system comprises a liquid and is maintained at about its boiling point in the reaction zone.

The reaction may be carried out in an apparatus comprising a vertical reactor containing a coalescer in the reaction zone, which may comprise the entire column or a portion thereof.

The process is more completely described in co-owned patent application having docket number CDT 1769/79 (U.S. Ser. No. 60/323,227 filed Sep. 14, 2001) which is hereby incorporated by reference.

The preferred alkylation process employs a downflow reactor packed with contacting internals or packing material (which may be inert or catalytic) through which passes a concurrent multi phase mixture of sulfuric acid, hydrocarbon solvent and reactants at the boiling point of the system. Adjusting the pressure and hydrocarbon composition controls the boiling point temperature. The reactor is preferentially operated vapor continuous but may also be operated liquid continuous. The pressure is preferentially higher at the top of the reactor than at the bottom. Adjusting the flow rates and the degree of vaporization controls the pressure drop across the reactor. Multiple injection of olefin is preferred. The product mixture before fractionation is the preferred circulating solvent. The acid emulsion separates rapidly from the hydrocarbon liquid and is normally recycled with only a few minutes residence time in the bottom phase separator. Because the products are in essence extracted from the acid emulsion, the reaction and/or emulsion promoters may be added without the usual concern for breaking the emulsion. The process may be described as being hydrocarbon continuous as opposed to acid continuous.

The coalescer comprises a conventional liquid-liquid coalescer of a type which is operative for coalescing vaporized liquids. These are commonly known as "mist eliminators" or "demisters". A suitable coalescer comprises a mesh such as a co-knit wire and fiberglass mesh. For example, it has been found that a 90 needle tubular co-knit mesh of wire and fiberglass such as manufactured by ACS Industries LLC of Houston, Tex., can be effectively utilized, however, it will be understood that various other materials such as co-knit wire and Teflon (Dupont™), steel wool, polypropylene, PVDF, polyester or various other co-knit materials can also be effectively utilized in the apparatus.

The invention claimed is:

1. A process for the utilization of refinery $C_4$ streams in the production of gasoline comprising the steps of:
   (a) feeding hydrogen and a mixed $C_4$ stream containing normal butane, isobutane, 1-butene, 2-butene, isobutene, dienes, mercaptans and $C_5$'s to a first distillation column reactor containing a bed of thioetherification/hydrogenation catalyst;
   (b) concurrently in said first distillation column reactor,
      (i) reacting the mercaptans and a portion of the dienes in the presence of said thioetherification/ hydrogenation catalyst to produce sulfides,
      (ii) reacting at least a portion of said dienes with said hydrogen to form mono olefins including additional butenes, and
      (iii) separating said sulfides and said $C_5$'s from said normal butane, isobutane, 1-butene, 2-butene and isobutene by fractional distillation;
   (c) removing said $C_5$'s and said sulfides from said first distillation column reactor as a first bottoms;
   (d) removing said normal butane, isobutane, 1-butene, 2-butene and isobutene from said first distillation column reactor as a first overheads;
   (e) feeding said first overheads containing said normal butane, isobutane, 1-butene, 2-butene and isobutene to a second distillation column reactor containing an bed of isomerization catalyst;
   (f) concurrently in said second distillation column reactor,
      (i) isomerizing a portion of the 1-butene to 2-butene, and
      (ii) separating the 2-butene and the normal butane from the isobutane, isobutene and unreacted 1-butene;
   (g) removing the 2-butene from said second distillation column reactor as a second bottoms;
   (h) removing the isobutane, unreacted 1-butene and isobutene from said second distillation column reactor as a second overheads;
   (i) feeding said hydrogen and second overheads containing said normal butane, isobutane, isobutene and 1-butene to a third distillation column reactor containing a bed of hydrogenation catalyst to concurrently;
      (i) hydrogenate a portion of the 1-butene and isobutene to form a reaction product comprising butane and isobutane and
      (ii) fractionate the reaction product to produce a third overheads; and
   (j) removing the normal butane, isobutane, 1-butene an isobutene from said third distillation column reactor as a third bottoms.

2. The process according to claim 1, wherein said second and third bottoms are fed to a cold acid alkylation unit.

3. The process according to claim 1, comprising recovering said third overheads comprising hydrogen, isobutane, 1-butene and isobutene; condensing said third overheads to recover a condensate comprising isobutane, 1-butene and returning said condensate to said third distillation column reactor as reflux.

4. The process according to claim 1, wherein said third distillation column reactor contains a bed of acidic cation exchange resin above said bed of hydrogenation catalyst and a portion of the isobutene is oligomerized to produce diisobutene which is hydrogenated in said bed of hydrogenation catalyst and said diisobutene is removed as a third bottoms and said isobutane, 1-butene and isobutene are removed as a third overheads.

5. The process according to claim 4 wherein said second bottoms and said third overheads are fed to a cold acid alkylation unit.

6. The process according to claim 4 wherein the normal butane, isobutane, 1-butene and isobutene is condensed and a portion is returned to said third distillation column reactor as reflux.

7. The process according to claim 1 wherein said hydrogenation is downflow.

* * * * *